(12) United States Patent
Matsumoto et al.

(10) Patent No.: US 9,682,204 B2
(45) Date of Patent: Jun. 20, 2017

(54) NON-HEATING TYPE FLAVOR INHALATOR AND METHOD OF MANUFACTURING FLAVOR CARTRIDGE

(71) Applicant: JAPAN TOBACCO INC., Tokyo (JP)

(72) Inventors: Hirofumi Matsumoto, Tokyo (JP); Takeshi Shinkawa, Tokyo (JP); Atsuro Yamada, Tokyo (JP); Kazuhiko Katayama, Tokyo (JP); Manabu Yamada, Tokyo (JP); Tomoichi Watanabe, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 953 days.

(21) Appl. No.: 13/774,830

(22) Filed: Feb. 22, 2013

(65) Prior Publication Data
US 2013/0160780 A1 Jun. 27, 2013

Related U.S. Application Data

(63) Continuation of application No. PCT/JP2011/069019, filed on Aug. 24, 2011.

(30) Foreign Application Priority Data

Aug. 24, 2010 (JP) .................................. 2010-187171

(51) Int. Cl.
  *A24F 47/00* (2006.01)
  *A61M 15/06* (2006.01)
  *B65B 1/20* (2006.01)

(52) U.S. Cl.
  CPC ........... *A61M 15/06* (2013.01); *A24F 47/002* (2013.01); *B65B 1/20* (2013.01); *A61M 2202/064* (2013.01)

(58) Field of Classification Search
CPC ....................................................... A24F 47/002
See application file for complete search history.

(56) References Cited

U.S. PATENT DOCUMENTS

| 4,836,225 A | 6/1989 | Sudoh |
| 5,101,838 A | 4/1992 | Schwartz |
| 7,726,320 B2 | 6/2010 | Robinson et al. |
| 2007/0267032 A1* | 11/2007 | Shan ................ A24F 47/002 131/275 |
| 2008/0241255 A1* | 10/2008 | Rose ................. A61K 31/4439 424/489 |

FOREIGN PATENT DOCUMENTS

| JP | 64-60364 A | 3/1989 |
| JP | 02-002331 A | 1/1990 |
| JP | 2-171174 A | 7/1990 |
| WO | WO 2010/095659 A1 | 8/2010 |
| WO | WO 2010/095660 A1 | 8/2010 |

* cited by examiner

*Primary Examiner* — Michael H Wilson
*Assistant Examiner* — Dionne Walls Mayes
(74) *Attorney, Agent, or Firm* — Birch, Stewart, Kolasch & Birch, LLP

(57) ABSTRACT

A non-heating type flavor inhalator of the invention includes a hollow cylindrical holder (2) having an ambient air admission opening (16) at a front end thereof and a mouthpiece end (4) at a rear end thereof, and a flavor cartridge (30) extending inside the holder (2) from the ambient air admission opening (16) toward the mouthpiece end (4) along the axis of the holder (2). The flavor cartridge (30) accommodates a flavor generating material (32) containing granular tobacco, and the flavor generating material (32) is kept in a predetermined required compressed state.

10 Claims, 21 Drawing Sheets

NON-HEATING TYPE FLAVOR INHALATOR AND METHOD OF MANUFACTURING FLAVOR CARTRIDGE

CROSS REFERENCE TO RELATED APPLICATIONS

This application is a Continuation of PCT International Application No. PCT/JP2011/069019 filed on Aug. 24, 2011, which claims priority under 35 U.S.C. §119(a) to Patent Application No. 2010-187171 filed in Japan on Aug. 24, 2010, all of which are hereby expressly incorporated by reference into the present application.

TECHNICAL FIELD

The present invention relates to a non-heating type flavor inhalator which need not be ignited and yet is capable of providing a user with a flavor component such as a tobacco flavor when the user inhales, and a method of manufacturing a flavor cartridge.

BACKGROUND ART

Cigarettes have long been articles of taste and beloved by many users. In recent years, attention has been directed to the problem that the sidestream smoke and odor emitted when a cigarette burns cause discomfort to people around the user.

To solve the problem, Patent Document 1 identified below provides a non-heating type flavor inhalator as smokeless tobacco. Specifically, the flavor inhalator includes an air-permeable tobacco molded article formed of a tobacco material and a binder, and a holder accommodating the tobacco molded article, the holder being in the form of a hollow cylinder and opening at both ends (Patent Document 1).

On the other hand, Patent Document 2, also identified below, discloses a flavor inhalator including a hollow cylindrical holder and a flavor cartridge accommodated in the holder. The flavor cartridge has a hollow cylindrical porous structure, and nicotine and a flavoring substance carried by the porous structure.

The flavor inhalators disclosed in Patent Documents 1 and 2 need not be ignited and yet can provide the user with a flavor component specific to tobacco when the user inhales the air that has passed through the tobacco molded article or the flavor cartridge.

PRIOR ART DOCUMENTS

Patent Documents

Patent Document 1: Japanese Laid-open Patent Publication No. 64-60364
Patent Document 2: Japanese Laid-open Patent Publication No. 2-171174

DISCLOSURE OF THE INVENTION

Problems to be Solved by the Invention

In the flavor inhalator of Patent Document 1, the area of contact between the tobacco material in the tobacco molded article and air is small, so that the amount of the flavor component emitted from the tobacco material into the air is small.

On the other hand, in the flavor inhalator of Patent Document 2, the porous structure has a large area of contact with air. Thus, compared with the flavor inhalator of Patent Document 1, the amount of the flavor component emitted from the porous structure into the air is large.

Even in the type of flavor inhalator disclosed in Patent Document 2, a tobacco material can be used in order to emit a flavor component similar to tobacco. In such case, if the tobacco material in the form of the aforementioned tobacco molded article is used, however, the amount of emission of the flavor component is small, as in the flavor inhalator of Patent Document 1. Consequently, the flavor component needs to be extracted from a tobacco material, and the porous structure needs to be impregnated with the extracted flavor component. The extraction process and the impregnation process, however, complicate the production of the flavor inhalator.

Further, the flavor inhalator of Patent Document 2 includes an air passage arranged downstream of the porous structure, and this air passage is relatively narrow and long. Accordingly, the flow velocity of air flowing through the air passage when the user inhales is relatively high, and such a fast flow of air produces a suction noise in the air passage. Depending upon the configuration of the air passage, the suction noise reverberates within the air passage, making the user feel strange.

Especially, where the internal passage through which the air having passed through the tobacco material flows is long as in the above flavor inhalator, generation and reverberation of suction noise are noticeable.

An object of the present invention is to provide a non-heating type flavor inhalator which ensures sufficiently high emission efficiency of a flavor component from tobacco material and which is also capable of effectively suppressing suction noise.

Means for Solving the Problems

In the non-heating type flavor inhalator disclosed in Patent Document 1, the tobacco molded article is formed by solidifying a tobacco material with the use of a binder. Accordingly, the area of contact between the tobacco material and air is small, and the emission efficiency of the flavor component from the tobacco material into the air is poor.

In the flavor inhalator of Patent Document 2, on the other hand, the porous structure containing the flavoring substance has a large area of contact with air. Thus, the emission efficiency of the flavor component from the porous structure is high, compared with the flavor inhalator of Patent Document 1.

In the case of the flavor inhalator of Patent Document 2, however, if a tobacco material is used in order to emit a flavor similar to tobacco, a large amount of binder needs to be used to solidify the tobacco material, with the result that the flavor emission efficiency lowers, as in the case of Patent Document 1. Consequently, extra processes are required to extract the flavor component from the tobacco material and to impregnate the porous structure with the extracted flavor component.

Further, after passing through the porous structure, the air is caused to flow through the relatively narrow and long air passage arranged downstream of the porous structure. Thus, the flow velocity of the air flowing through the air passage is relatively high. Such a fast flow of air in the air passage produces a suction noise, and depending on the configuration of the air passage, the suction noise reverberates within the air passage, making the user feel strange.

An object of the present invention is to provide a non-heating type flavor inhalator which ensures sufficiently high emission efficiency of a tobacco flavor component from a flavor generating material and which is also capable of effectively suppressing suction noise, and a method of manufacturing a flavor cartridge.

The object is achieved by a non-heating type flavor inhalator of the present invention, which comprises:

a hollow holder having an axis, the holder including a front end, a rear end serving as a mouthpiece end, an ambient air admission opening, and a flow passage defined in the holder and configured to guide ambient air introduced from the ambient air admission opening to the mouthpiece end; and a flavor cartridge having air permeability and arranged in the holder so as to extend inside the holder from the front end toward the mouthpiece end along the axis of the holder, the flavor cartridge dividing the flow passage into a downstream region extending from the flavor cartridge to the mouthpiece end, and an upstream region communicating with the ambient air admission opening and located contiguous with the flavor cartridge, wherein the flavor cartridge includes
a frame,
a granular flavor generating material filled in the frame and capable of emitting a flavor component without being ignited, the flavor generating material containing granular tobacco obtained by shredding or pulverizing tobacco leaf, and a compression device configured to keep the flavor generating material in a compressed state while ensuring air permeability of the flavor cartridge.

With the above flavor inhalator, when the user inhales through the mouthpiece end of the holder, air passes through the flavor cartridge uniformly over its entire area. At this time, the air is allowed to satisfactorily contact with the flavor generating material in the flavor cartridge and thus can contain the tobacco flavor component emitted from the flavor generating material. Since the air inhaled by the user contains the tobacco flavor component, the user can effectively enjoy the tobacco flavor.

Also, the flavor generating material is kept in the compressed state, and therefore, the flavor generating material serves also as a sound absorbing wall for damping the aforementioned suction noise and effectively suppresses generation of the suction noise.

Specifically, the compression device includes a pair of compression elements configured to compress the flavor generating material in a direction perpendicular to the axis of the holder, and each of the compression elements has a plurality of ventilation openings formed therein to secure air permeability of the flavor cartridge. Preferably, in this case, the ventilation openings in one of the compression elements partly overlap with those in the other of the compression elements, as viewed in the direction of compression of the flavor generating material.

Further, the flavor generating material is preferably filled in such a manner that a flow resistance of the flavor generating material after compression, expressed by a formula:

$$((1-\text{Porosity}^2)/\text{Porosity}^3) \times (\text{Filling height}/\text{Sectional area})$$

is equal to or higher than 0.005.

The flavor cartridge may further include an air-permeable pouch wrapping the flavor generating material therein, or where the flavor generating material is filled directly in the frame, the flavor cartridge may further include an air-permeable element covering the ventilation openings of the compression elements.

Preferably, the air-permeable pouch and the air-permeable element have a pressure loss of 0.5 mmH$_2$O or higher.

The present invention also provides a method of manufacturing the aforementioned flavor cartridge. The method, other objects of the present invention and the detailed construction of the flavor inhalator will become apparent from the detailed description given below.

Advantageous Effects of the Invention

The non-heating type flavor inhalator according to the present invention permits the tobacco flavor component to be effectively emitted from the flavor cartridge and is also capable of suppressing generation of the suction noise.

BEST MODE OF CARRYING OUT THE INVENTION

Figure 1:
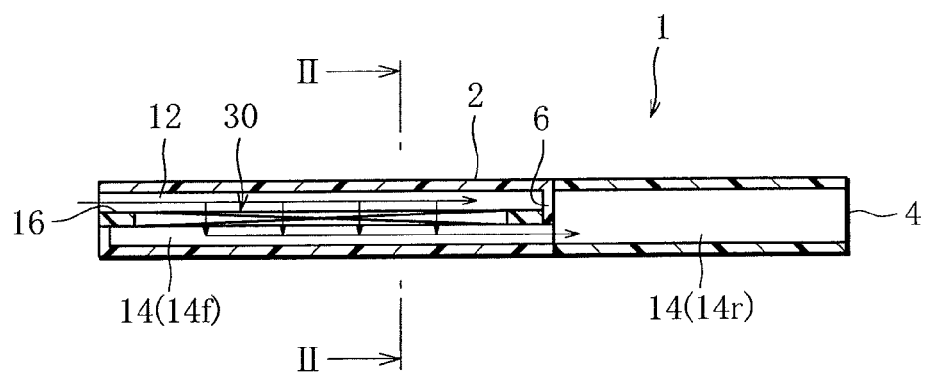
FIG. 1 is a sectional view of a flavor inhalator according to a first embodiment.

Referring to FIG. 1, there is illustrated a non-heating type flavor inhalator 1 (hereinafter merely referred to as inhalator) of a first embodiment provided with a holder 2 of synthetic resin. The holder 2 is in the form of a hollow cylinder and has a rear open end and a front open end. The rear end forms a mouthpiece end 4, and the front end is open only in its upper half. The semicircular opening forms an ambient air admission opening 16. Thus, a flow passage extending from the ambient air admission opening 16 to the mouthpiece end 4 is formed within the holder 2.

Preferably, the holder 2 has an inner diameter ranging from 4 to 14 mm. The holder 2 may alternatively have an elliptical cross-sectional shape, and in this case, the major axis of the ellipse preferably has a length ranging from 4 to 14 mm.

A semicircular partition wall 6 protrudes from the inner peripheral surface of the holder 2 and is located so as to be closer to the mouthpiece end 4 than the center of the holder 2 is, as viewed in the axial direction of the holder 2. The partition wall 6 closes a semicircular region corresponding to approximately the half of the cross section of the holder 2.

Figure 2:
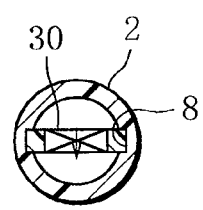
FIG. 2 is a sectional view of the flavor inhalator taken along line II-II in FIG. 1.

Further, as clearly shown in FIG. 2, a pair of longitudinal grooves 8 are formed in the inner peripheral surface of the holder 2. The longitudinal grooves 8 are set apart from each other in a diametrical direction of the holder 2 with the axis of the holder 2 located therebetween and extend from the projecting end of the partition wall 6 to the front end of the holder 2 in parallel with the axis of the holder 2.

A flavor cartridge 30 is arranged inside the holder 2. The flavor cartridge 30 extends from the front end of the holder 2 to the partition wall 6 in alignment with the axis of the holder 2 and has a pair of side edges fitted into the respective longitudinal grooves 8. That is, the flavor cartridge 30 is supported by the holder 2. Specifically, the flavor cartridge 30 is in the form of a plate and has a width slightly larger than the inner diameter of the holder 2, that is, a width nearly equal to the distance between the bottoms of the two longitudinal grooves 8.

In this embodiment, the flavor cartridge 30 and the partition wall 6 divide the flow passage in the holder 2 into an upstream region 12 and a downstream region 14. The upstream region 12 is located close to the front end of the holder 2 and extends from the ambient air admission opening 16 to the partition wall 6, as viewed in the axial direction of the holder 2. With respect to the radial direction of the holder 2, the upstream region 12 is defined by the semi-circumferential inner peripheral surface of the holder 2 and the flavor cartridge 30. Accordingly, the upstream region 12 has a semicircular cross-sectional flow area.

On the other hand, the downstream region 14 extends from the front end to the mouthpiece end 4 of the holder 2 and has a front flow section 14f and a rear flow section 14r. Specifically, the front flow section 14f extends from the front end of the holder 2 to the partition wall 16 and faces the upstream region 12 with the flavor cartridge 30 interposed therebetween. Thus, the front flow section 14f has a semicircular cross-sectional flow area, like the upstream region 12. As a consequence, the flavor cartridge 30 has rectangular exposure areas exposed to the upstream region 12 and the front flow section 14f, respectively, and each exposure area is substantially larger than the cross-sectional area of the holder 2. The rear flow section 14r has a circular cross-sectional flow area and extends from the partition wall 16 to the mouthpiece end 4.

Figure 3:
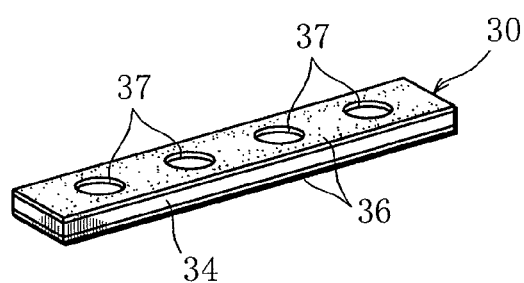
FIG. 3 is a perspective view of a flavor cartridge shown in FIG. 1.
Figure 4:
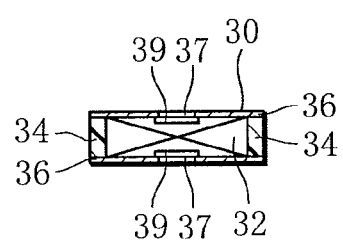
FIG. 4 is a sectional view of the flavor cartridge.

As illustrated in FIGS. 3 and 4, the flavor cartridge 30 includes a rectangular frame 34 and a flavor generating material 32 filled directly in the frame 34. The flavor generating material 32 contains granular tobacco as its main constituent, and the granular tobacco is obtained by shredding or pulverizing tobacco leaf and has a grain size of 0.2 to 2.0 mm.

Preferably, the flavor generating material 32 further contains an additive such as carbonate or hydrogencarbonate of alkali metal or alkaline-earth metal, and such additive promotes the emission of a flavor component from the granular tobacco. Where the additive is potassium carbonate, for example, calcium carbonate is preferably contained in an amount of 1 to 10 weight % with respect to the dry weight of the granular tobacco.

The flavor generating material 32 contains no binder, and therefore, the granular tobacco in the flavor generating material 32 has a sufficiently large area of contact with air. Thus, although no heat is applied to the granular tobacco of the flavor generating material 32, a sufficient amount of the flavor component can be emitted from the granular tobacco. The flavor generating material 32 may contain a flavoring other than the granular tobacco, and such additional flavoring may emit a flavor component different from that of the granular tobacco.

Thus, the frame 34, which may be made of a general-purpose resin such as polypropylene (PP), is preferably made of a material which is less likely to take on the flavor components of the granular tobacco and additional flavoring. A preferred example of the material of the frame 34 is ethylene-vinyl alcohol copolymer (trademark: EVOH), but paper may also be used.

The flavor cartridge 30 further includes a pair of compression elements, namely, compression plates 36. These compression plates 36 constitute upper and lower lids of the frame 34, respectively, and serve to keep the flavor generating material 32 in a predetermined required compressed state. The required compressed state will be explained later. The compression plates 36 are also disposed in direct contact with the flavor generating material 32, and therefore, the compression plate 36 are preferably made of the same material as the frame 34.

A plurality of ventilation openings 37 are formed through each compression plate 36 to ensure air permeability of the flavor cartridge 30 irrespective of the presence of the compression plates 36. Specifically, the ventilation openings 37 of one compression plate 36 preferably overlap at least partly with the respective ventilation openings 37 of the other compression plate 36 (see FIG. 4).

The ventilation openings 37 secure the air permeability of the flavor cartridge 30 as stated above, but since the main constituent of the flavor generating material is granular tobacco, the granular tobacco can drop through the ventilation openings 37, making it difficult to maintain the required compressed state. In this regard, the formation of the ventilation openings 37 is not preferred.

Thus, according to this embodiment, each ventilation opening 37 is covered with an air-permeable sheet 39 as an air-permeable element, and the air-permeable sheet 39 has a pressure loss of 0.5 mmH$_2$O or higher. Specifically, the air-permeable sheet 39 is made of nonwoven cloth, mesh sheet or the like, and in this case, the air-permeable sheet 39 may be affixed to the compression plate 36 by an adhesive. Preferably, the air-permeable sheet 39 is made of or coated with the same material as the compression plate 36, in which case the air-permeable sheet 39 can be affixed to the compression plate 36 by thermal welding or ultrasonic welding.

Figure 5:
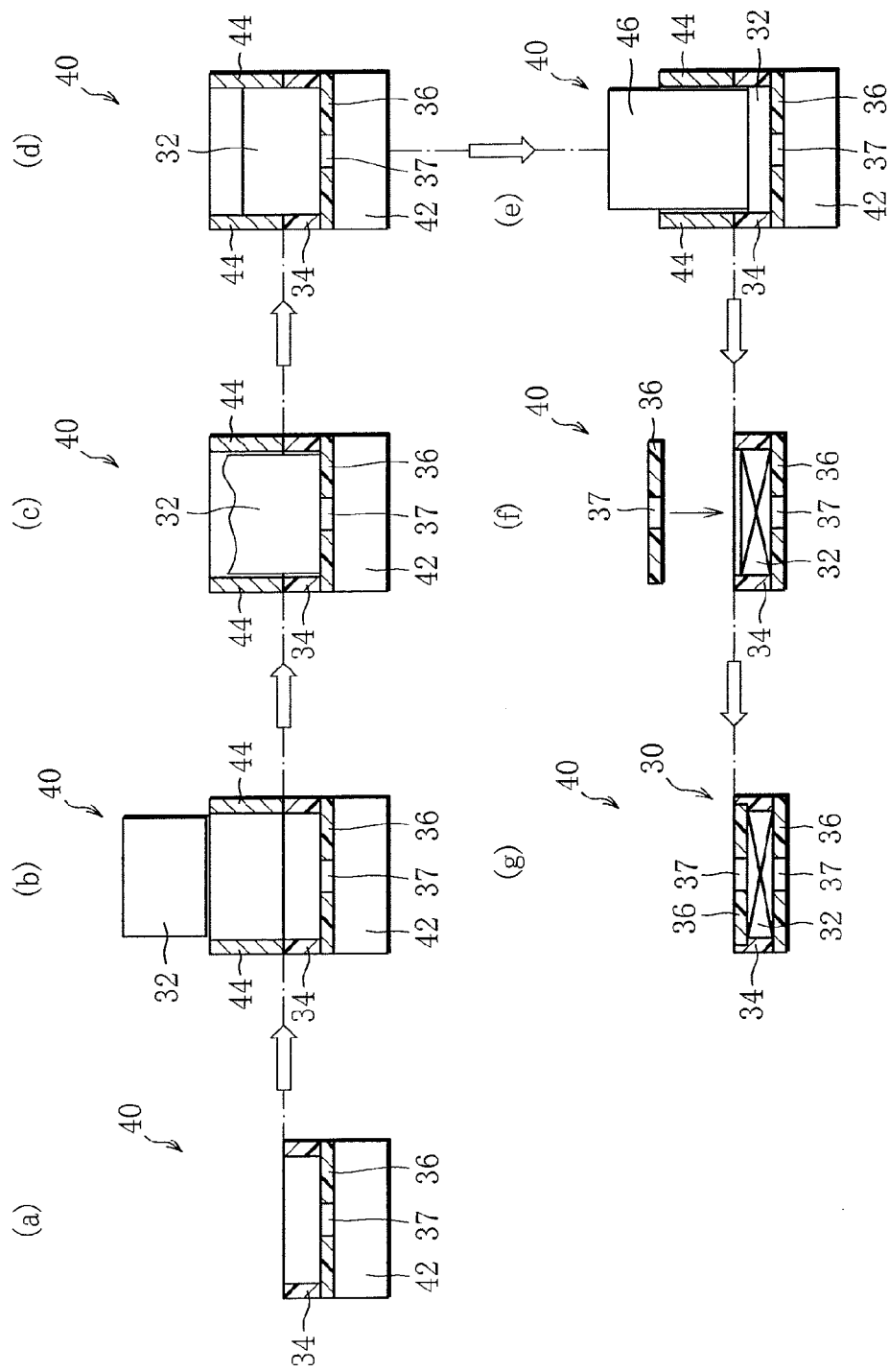
FIGS. 5(a) to 5(g) illustrate a procedure for producing the flavor cartridge in order.

FIG. 5 schematically illustrates an apparatus for manufacturing the flavor cartridge 30 and a manufacturing procedure.

The manufacturing apparatus 40 has a supporting base 42, and the frame 34 and the lower compression plate 36 already provided with the air-permeable sheet 39 are placed on the supporting base 42 (FIG. 5(a)). At this point, the frame 34 and the lower compression plate 36 are already joined together. In FIG. 5, the air-permeable sheet 39 is omitted.

The manufacturing apparatus 40 further includes a guide frame 44 and a pusher 46. The guide frame 44 has an internal shape coinciding with that of the frame 34. Accordingly, when placed on the frame 34, the guide frame 44 forms an extension section of the frame 34 (FIG. 5(b)).

On the other hand, the pusher 46 has such a size as to be fittable into the guide frame 44 and is vertically movable inside the guide frame 44 and the frame 34 (FIG. 5(e)).

To produce the flavor cartridge 30, first, a predetermined amount of the flavor generating material 32 measured beforehand is filled in the interior of the frame 34 through the guide frame 44 (FIG. 5(b)). At this time, the flavor generating material 32 is filled up to a height, or a filling height, such that the upper surface thereof is located above the frame 34, that is, within the guide frame 44 (FIG. 5(c)). Subsequently, the surface of the flavor generating material 32 is flattened as needed (FIG. 5(d)).

With the flavor generating material 32 thus filled, the pusher 46 is inserted into the guide frame 44 from above the guide frame 44 to compress the flavor generating material 32 within the frame 34 into an over-compressed state, which is a more strongly compressed state than the aforementioned required compressed state. Subsequently, the pusher 46 and the guide frame 44 are returned to a rest position set above the frame 34, and immediately thereafter, the upper compression plate 36 already provided with the air-permeable sheet 39 is attached to the upper surface of the frame 34. At this point, the production of the flavor cartridge 30 is completed (FIG. 5(e)).

The aforementioned required compressed state of the flavor generating material 32 created by the pusher 46 provides a bulk density ranging from 150 to 2500 mg/cc to the flavor generating material 32. Specifically, the bulk density of the compressed flavor generating material 32 is 1.5 to 5 times the bulk density of the uncompressed flavor generating material 32. For example, where the frame 34 has an opening area of 100 to 1000 mm$^2$ and a height of 1 to 6 mm, the filling content of the flavor generating material 32 is 100 to 1000 mg. The flavor generating material 32 filled in such an amount makes it possible for the flavor generating material 32 to maintain the predetermined required compressed state within the frame 34, that is, within the flavor cartridge 30, and at the same time to exhibit sufficient air permeability. Consequently, uneven distribution of the flavor generating material 32 within the frame 34 can be reliably prevented.

When the upper compression plate 36 is attached, the flavor generating material 32 is in a state released from the compression by the pusher 46. Thus, although the flavor generating material 32 expands from the over-compressed state, the material 32 keeps an intermediate compressed state between the over-compressed state and the required compressed state, providing a gap between the surface of the flavor generating material 32 and the upper compression plate 36.

Accordingly, when the upper compression plate 36 is attached, the flavor generating material 32 is reliably prevented from intervening between the upper compression plate 36 and the frame 34. Even after the upper compression plate 36 is attached, the flavor generating material 32 keeps expanding, but the expansion stops when the surface of the flavor generating material 32 reaches the upper compression plate 36. As a result, the flavor generating material 32 is kept in the required compressed state.

As will be clear from the above explanation of the manufacturing apparatus 40 with reference to FIG. 5, the lower compression plate 36 may be formed as an integral part of the frame 34.

The manufacturing apparatus 40 of FIG. 5 may further include a suction mechanism for suppressing the expansion of the flavor generating material 32 after the material 32 is released from the compression. Specifically, the suction mechanism has a plurality of suction nozzles (not shown). The suction nozzles are located at the respective ventilation openings 37 of the lower compression plate 36 and are connected to a suction source. The suction nozzles suck in air from inside the frame 34, and because of the suction of the air, the flavor generating material 32 is pulled toward the lower compression plate 36, thus suppressing the expansion of the flavor generating material 32. In this case, extra time can be spared for the attachment of the upper compression plate 36 to the frame 34.

With the flavor inhalator 1 of the first embodiment, when the user inhales through the mouthpiece end 4 of the holder 2, ambient air enters the upstream region 12 from the ambient air admission opening 16 of the holder 2, then flows into the flavor cartridge 30 from the entire area of the upstream region in the radial direction of the holder 2, and reaches the downstream region 14, as indicated by the arrows in FIG. 1. That is, the air passes through the flavor cartridge 30 uniformly over the entire large area of the flavor cartridge 30 extending in the axial direction of the holder 2.

Consequently, the air can be made to satisfactorily contact with the flavor generating material 32 (granular tobacco) in the flavor cartridge 30 and effectively contain the flavor component emitted from the granular tobacco. The air containing the flavor component is then guided from the downstream region 14 to the mouthpiece end 4 and reaches the user's mouth.

Since the air inhaled by the user contains a sufficient amount of the flavor component, the user can enjoy the tobacco flavor in an effective manner.

When the user inhales through the flavor inhalator 1 as stated above, the flow of air within the holder 2 may possibly produce a suction noise. With the flavor inhalator 1 of the present invention, such suction noise can be effectively suppressed.

Specifically, the flavor generating material 32 contained in the flavor cartridge 30 is kept in the aforementioned required compressed state and thus serves also as a sound absorbing wall for damping the suction noise, whereby generation of the suction noise can be effectively suppressed.

Further, the flavor cartridge 30 is supported inside the holder 2 while being securely fitted in the longitudinal grooves 8. Air is therefore unable to make a detour through gaps between the flavor cartridge 30 and the longitudinal grooves 8, whereby leak of the noise attributable to such detour of air can also be reliably prevented.

Furthermore, the flavor inhalator 1 can be configured to have a size and a shape similar to those of an ordinary cigarette, so that the user can use the flavor inhalator 1 just as if he/she were smoking an ordinary cigarette.

Figure 6:
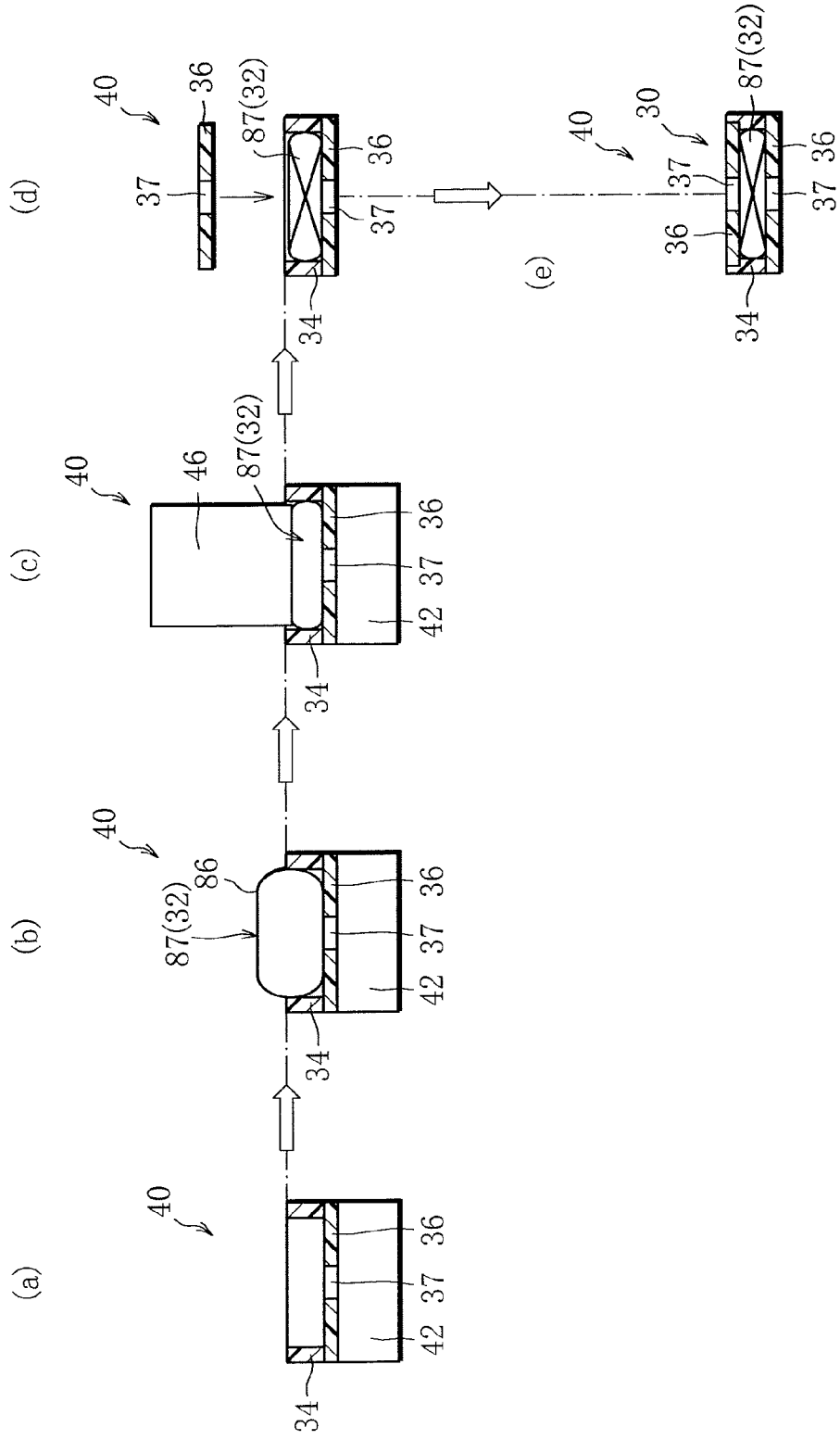
FIGS. 6(a) to 6(e) illustrate a procedure for producing a flavor cartridge of a second embodiment in order.

FIG. 6 schematically illustrates a flavor cartridge 30 used with a flavor inhalator 1 according to a second embodiment and a manufacturing apparatus therefor.

The flavor cartridge 30 further includes an air-permeable pouch 86 wrapping the flavor generating material 32 therein, and the flavor generating material 32 and the air-permeable pouch 86 form a flavor pack 87. The air-permeable pouch 86 is made of nonwoven cloth, like the aforementioned air-permeable sheet 39, and has a pressure loss of 0.5 mmH$_2$O or higher.

In the case of the second embodiment, each compression plate 36 need not be provided with the air-permeable sheet 39.

Following the procedure described below, the manufacturing apparatus 40 shown in FIG. 6 produces the flavor cartridge 30.

First, the frame 34 is placed on the supporting base 42 (FIG. 6(a)), and the prepared flavor pack 87 is put in the frame 34 (FIG. 6(b)). Subsequently, the flavor pack 87 is compressed by the pusher 46 into the over-compressed state (FIG. 6(c)). After the flavor pack 87 is released from the compression by the pusher 46, the upper compression plate 36 is attached to the frame 34 (FIG. 6(d)). At this point, the production of the flavor cartridge 30 is completed (FIG. 6(e)), and the flavor generating material 32 of the flavor pack 87 is kept in the required compressed state.

Like the compressed flavor generating material 32 of the first embodiment, the flavor pack 87 of the second embodiment also provides a sound absorption effect.

Figure 7:
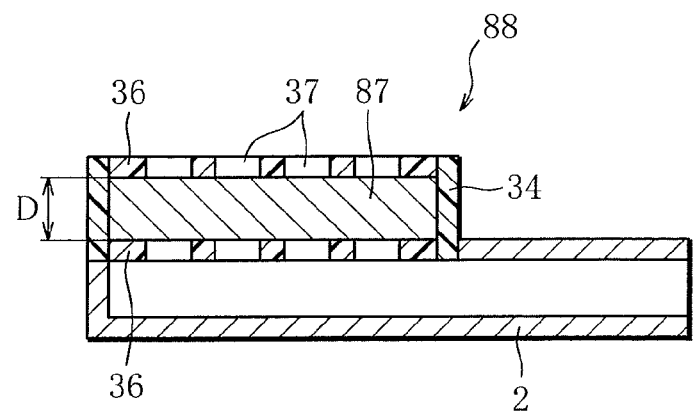
FIG. 7 is a sectional view of a suction tester.
Figure 8:
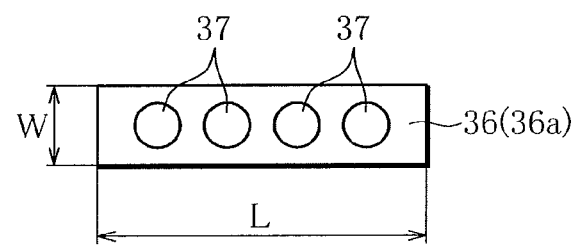
FIG. 8 is a plan view of a compression plate used in the suction tester of FIG. 7.

To verify the sound absorption effect of the flavor pack 87, namely, the flavor generating material 32, a suction tester 88 illustrated in FIG. 7 was prepared.

Specifications of the suction tester 88 are as follows:
Material of the air-permeable pouch 86: polyolefin nonwoven cloth (HOP-30H from Hirose Paper Manufacturing Co., Ltd.)

The number in "HOP-30H" indicates metsuke, or weight per unit area (g/mm$^2$).

Size of the air-permeable pouch 86: 11 mm×50 mm

Flavor generating material 32: granular tobacco (Japanese-grown burley) screened using a sieve of 0.2 mm to 1.18 mm Bulk density=142 mg/cc, Apparent density=550 mg/cc Filling content of the flavor generating material 32: 200 mg, 300 mg Internal size of the frame 34: 10 mm×50 mm Effective depth D of the frame 34 (distance between the upper and lower compression plates 36): 2 mm, 3 mm, 4 mm Size of the upper and lower compression plates 36a: Length L=50 mm, Width W=10 mm Size, number, and arrangement of the ventilation openings 37 in each compression plate 36a: 4 circular holes with a diameter of 7 mm, arranged at a pitch of 10 mm Table 1 below shows the results of suction tests conducted repeatedly by a plurality of evaluators for the evaluation of suction noise, using the tester illustrated in FIG. 7.

TABLE 1

| D | 2 mm | 3 mm | 4 mm |
|---|---|---|---|
| Effective capacity of frame | 1.0 cc | 1.5 cc | 2.0 cc |
| Filling content = 200 mg | Not so annoying | Annoying | — |
| Filling content = 300 mg | Not annoying | Not so annoying | Somewhat annoying |

As is clear from the results shown in Table 1, with respect to the same filling content of the flavor generating material 32, the suction noise is less annoying when the effective capacity of the frame (capacity surrounded by the frame 34 and the two compression plates 36a) is smaller, that is, when the density of the compressed flavor generating material 32 is higher. This means that compressing the flavor generating material 32 is effective in lessening the suction noise.

Also, the influence of the ventilation openings 37 of the compression plates 36 on the delivery of tobacco component (nicotine) from the flavor generating material 32 to air was verified.

Figure 9:
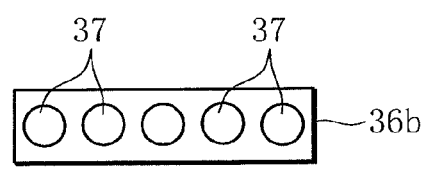
FIG. 9 is a plan view of another compression plate.
Figure 10:
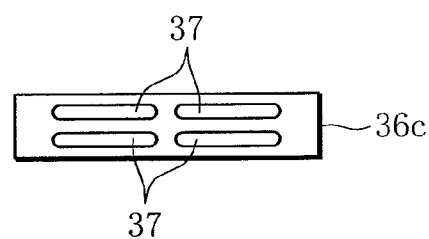
FIG. 10 is a plan view of still another compression plate.

For the purpose of verification, compression plates 36b and 36c illustrated in FIGS. 9 and 10, respectively, were newly prepared. The compression plate 36b differs from the compression plate 36a only in that it has five ventilation openings 37. The compression plate 36c has elongate ventilation openings 37, in place of the circular ventilation openings. The elongate ventilation openings 37 each have a size of 2.4 mm×14.6 mm and are distributed in 2×2 form in a central region of the compression plate 36.

The suction tester 88 of FIG. 7 was used separately as suction testers 88a, 88b and 88c according to the combination of the compression plates 36 used. The suction testers 88a, 88b and 88c were used with the following combinations of the compression plates 36:

TABLE 2

|  | Suction tester 88a | Suction tester 88b | Suction tester 88c |
|---|---|---|---|
| Upper compression plate | 36a | 36a | 36a |
| Lower compression plate | 36a | 36b | 36c |

For all of the suction testers 88a, 88b and 88c, the frame 34 with an effective depth D of 2 mm was used, and the flavor pack 87 was accommodated in the frame 34. The flavor generating material 32 of the flavor pack 87 used was a mixture of granular tobacco and granular potassium carbonate as an additive, and the weight of the mixture was 200 mg. The granular tobacco was obtained by pulverizing Japanese-grown burley tobacco leaf and screening the obtained granules with the use of a sieve of 0.5 mm to 1.18 mm.

Figure 11:
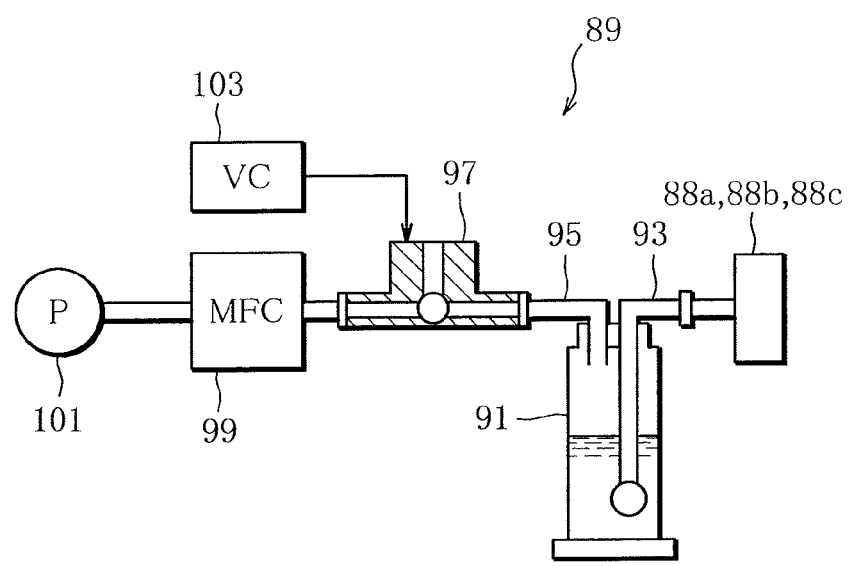
FIG. 11 schematically illustrates a measuring device used with the suction tester of FIG. 7.

Further, to measure the amount of delivery of tobacco component, that is, nicotine, from the flavor generating material 32 to air, a measuring device 89 shown in FIG. 11 was used.

The measuring device 89 is provided with an impinger 91 containing 20 ml of ethanol. Specifically, for the impinger 91, a Kinoshita-type gas absorption washing bottle (standard type: 50 ml) from Kinoshita Rika Kogyo Kabushiki Kaisha was used. The impinger 91 contains filter particles (100 to 200 μm) and has a suction tube 93 and a delivery tube 95 extending from inside the impinger 91.

The suction tube 93 is connected to the mouthpiece end 4 of the holder 2 of the suction tester 88, and the delivery tube 95 is connected to a suction pump 101 via a solenoid valve 97 and a mass flow controller (MFC) 99. The solenoid valve 97 is electrically connected to a valve controller (VC) 103, which controls the opening/closing operation of the solenoid valve 97.

Specifically, the solenoid valve 97 is opened and closed by the valve controller 103 to repeat a puff cycle. The puff cycle includes a 4-second suction period for which the impinger 91 is connected to the suction pump 101, and an 11-second rest period for which the impinger 91 is opened to the atmosphere. The flow rate of the mass flow controller 99 was set to 3300 cc/min.

With the suction tube 93 of the impinger 91 connected to one of the suction testers 88a, 88b and 88c, the puff cycle was repeated 50 times in an environment of the room temperature 22° C. and the humidity 60%. Nicotine delivered from the flavor pack 87 into the suction air was collected by the ethanol contained in the impinger 91.

Subsequently, the ethanol containing nicotine was emptied out of the impinger 91 into a gas chromatography mass spectrometer for analysis, and the amount of delivery of nicotine from the suction tester 88 per puff cycle (one puff) was measured.

The collection, analysis and measurement of nicotine were repeatedly executed, and the measurement process for the suction tester 88 was terminated when the number of puff cycles reached a predetermined number.

The measurement process was conducted with respect to each suction tester 88. The measurement results are shown in FIG. 12.

Figure 12:
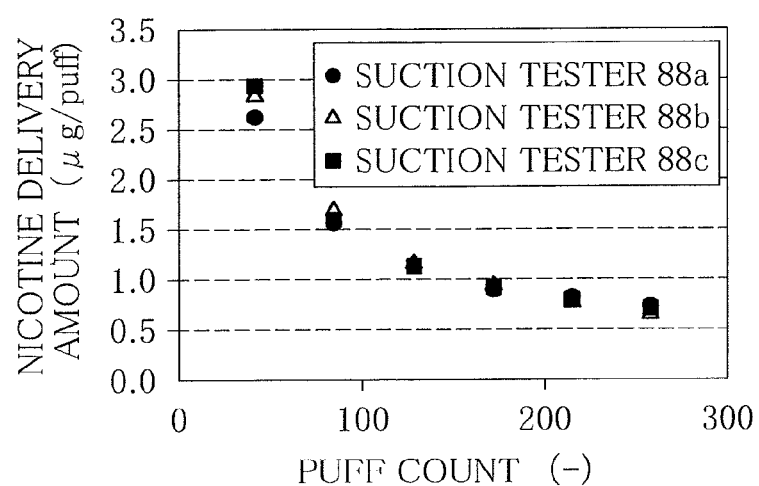
FIG. 12 is a graph showing the relationship between puff count and nicotine delivery amount.

As is clear from FIG. 12, the measurement results of the suction testers 88a, 88b and 88c show little difference. Generally, the ventilation openings 37 of the upper and lower compression plates 36 are arranged symmetrically with the flavor pack 87 therebetween, as in the suction tester 88a. However, even if the ventilation openings 37 of the upper and lower compression plates 36 are arranged in an asymmetric manner as in the suction testers 88b and 88c, no difference is observed between the suction tester 88a and the suction testers 88b and 88c with regard to the nicotine delivery amount and change in the delivery amount with increase in the puff count.

Arranging the ventilation openings 37 asymmetrically means that the compressed surface regions of the flavor pack 87 (flavor generating material 32) compressed by the upper and lower compression plates 36 are asymmetric, so that the pressure applied to the flavor generating material 32 is dispersed. Such pressure dispersion is effective in maintaining the required compressed state of the flavor generating material 32.

Where the flow of air within the flavor generating material 32 is taken into consideration, however, completely asymmetric arrangement of the ventilation openings 37 leads to increase in regions where the air keeps still within the flavor generation material 23, deteriorating the delivery of the tobacco component to the air. Thus, it is preferable that the upper and lower ventilation openings 37 be arranged so as to partly overlap with each other, as stated above.

Figure 13:
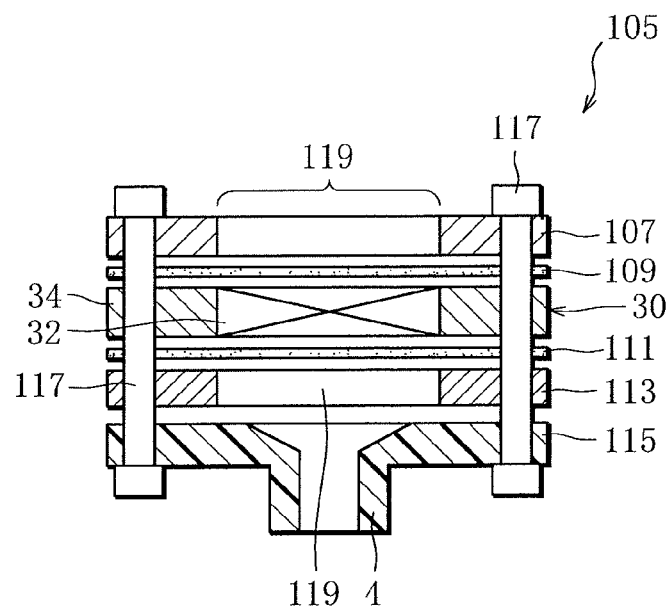
FIG. 13 is a sectional view of another suction tester.

In order to verify the sound absorption effect provided by the compression of the flavor generating material 32, a suction tester 105 illustrated in FIG. 13 was prepared.

The suction tester 105 has an axis and includes an upstream-side member 107, a mesh member 109, a frame 34, a mesh member 111, a downstream-side member 113 and a mouthpiece member 115 aligned with the axis in the mentioned order and combined together into a unit by a plurality of connecting bolts and nuts 117.

Specifically, each of the upstream- and downstream-side members 107 and 113 is a stainless steel sheet with a thickness of 2 mm and has a circular opening 119 in the center thereof. The openings 119 have a size equal to the inner diameter of the frame 34.

Each of the mesh members 109 and 111 is made of stainless steel wires with a diameter of 0.1 mm and has a size of openings, or a mesh size, of 100. Accordingly, the pressure loss of the mesh members 109 and 111 are infinitely close to zero. The mesh members 109 and 111 correspond to the compression plates 36 of the flavor cartridge 30.

For the frame 34, a plurality of frames with different sizes were prepared and were filled with granular tobacco so as to have three different filling contents.

Specifically, the flavor cartridge 30 is constituted by the mesh members 109 and 111, the frame 34 and the granular tobacco, and three flavor cartridges 30a, 30b and 30c having three different filling contents of granular tobacco were prepared. The flavor cartridges 30a, 30b and 30c had filling contents of 100 mg, 200 mg, and 300 mg, respectively.

The mouthpiece member 115 is made of Teflon (registered trademark) and has a mouthpiece end 4. Inner and outer diameters of the mouthpiece end 4 were 6 mm and 8 mm, respectively.

With the flavor cartridge 30a set in the suction tester 105, a suction test was conducted by a plurality of testing persons, and the suction noise from the suction tester 105 was evaluated by a plurality of evaluators at a distance of 50 cm from the testing person, together with unevenness of the granular tobacco in the flavor cartridge 30. The evaluation results are shown in Table 3 below.

Also, the suction testers 105 fitted with the flavor cartridges 30b and 30c were evaluated in the same manner, the evaluation results being shown in Tables 4 and 5, respectively.

TABLE 3

| Filling weight | | Suction noise Height (mm) | | | | Unevenness Height (mm) | | | | Compression ratio Height (mm) | | | |
|---|---|---|---|---|---|---|---|---|---|---|---|---|---|
| 100 mg | | 2 | 4 | 4 | 5 | 2 | 4 | 4 | 5 | 2 | 4 | 4 | 5 |
| Inner diameter of frame (mm) | 10 | | | ○ | | | | ○ | | 76% | 67% | 55% | 44% |
| | 12 | | ○ | ○ | | | | ○ | ○ | 68% | 52% | 36% | 20% |
| | 14 | | ○ | ○ | Δ | | ○ | ○ | X | 56% | 34% | 13% | |
| | 16 | ○ | Δ* | X | X | ○ | ○* | X | | 43% | 14% | | |
| | 18 | Δ* | X | | | ○ | X* | | | 28% | | | |
| | 20 | X | | | | X | | | | 11% | | | |
| | 22 | X | | | | X | | | | | | | |
| | 24 | | | | | | | | | | | | |
| | 26 | | | | | | | | | | | | |
| | 28 | | | | | | | | | | | | |
| | 30 | | | | | | | | | | | | |

TABLE 4

| Filling weight | | Suction noise Height (mm) | | | | Unevenness Height (mm) | | | | Compression ratio Height (mm) | | | |
|---|---|---|---|---|---|---|---|---|---|---|---|---|---|
| 200 mg | | 2 | 3 | 4 | 5 | 2 | 3 | 4 | 5 | 2 | 3 | 4 | 5 |
| Inner diameter of frame (mm) | 10 | | | | | | | | | 86% | 83% | 78% | 72% |
| | 12 | | | | | | | | | 84% | 76% | 68% | 60% |
| | 14 | | | ○ | | | | | ○ | 78% | 67% | 56% | 45% |
| | 16 | | ○ | ○ | ○ | | ○ | ○ | ○ | 71% | 57% | 43% | 29% |
| | 18 | | ○ | ○ | Δ* | | ○ | ○ | ○* | 64% | 46% | 28% | 10% |
| | 20 | ○ | ○ | Δ* | X | | ○ | ○* | X | 55% | 33% | 11% | |
| | 22 | ○ | X* | X | | ○ | ○* | X | | 46% | 19% | | |
| | 24 | X* | X | | | ○* | X | | | 36% | 4% | | |
| | 26 | X* | | | | ○* | | | | 25% | | | |
| | 28 | X | | | | X | | | | 13% | | | |
| | 30 | | | | | | | | | | | | |

TABLE 5

| Filling weight | | Suction noise Height (mm) | | | | Unevenness Height (mm) | | | | Compression ratio Height (mm) | | | |
|---|---|---|---|---|---|---|---|---|---|---|---|---|---|
| 300 mg | | 2 | 3 | 4 | 5 | 2 | 4 | 4 | 5 | 2 | 3 | 4 | 5 |
| Inner diameter of frame (mm) | 10 | | | | | | | | | 93% | 89% | 85% | 81% |
| | 12 | | | | | | | | | 89% | 84% | 79% | 73% |
| | 14 | | | | | | | | | 85% | 78% | 71% | 64% |
| | 16 | | | ○ | | | | | ○ | 81% | 71% | 62% | 52% |
| | 18 | | | ○ | ○ | | | ○ | ○ | 76% | 64% | 52% | 40% |
| | 20 | | ○ | ○ | ○ | | ○ | ○ | ○ | 70% | 55% | 41% | 26% |
| | 22 | | ○ | ○ | Δ* | | ○ | ○ | ○* | 64% | 46% | 28% | 10% |
| | 24 | | ○ | X* | X | | ○ | ○* | X | 57% | 36% | 14% | |
| | 26 | ○ | X* | X | | ○ | ○* | X | | 50% | 25% | | |
| | 28 | X* | X | | | ○* | X | | | 42% | 13% | | |
| | 30 | X* | X | | | ○* | X | | | 33% | | | |

Regarding the evaluation of the suction noise in Tables 3 to 5, "o", "Δ" and "x" respectively indicate "not annoying", "somewhat annoying", and "annoying".

Unevenness of the granular tobacco was evaluated in the following manner:

With the suction tester 105 held horizontally, the evaluator tapped the suction tester 105 ten times from a location 2 cm above the suction tester 105 and then confirmed whether or not a space was created inside the frame 34, that is, whether the granular tobacco was uneven or not. In Tables 3 to 5, "o" indicates "even", and "x" indicates "uneven".

With regard to the evaluation of the suction noise and unevenness in Tables 3 to 5, the blanks indicate that no evaluation was made.

Further, in Tables 3 to 5, the compressed states of the granular tobacco under the respective conditions are shown under "Compression ratio". The compression ratio was derived according to the following formula:

Compression ratio (%)=(1−Filling capacity inside frame/Filling volume of granular tobacco in natural state)×100

Filling volume of granular tobacco in natural state=Filling weight/Bulk density

Regarding the compression ratio in Tables 3 to 5, the blanks indicate that the granular tobacco was not compressed.

Tables 3 to 5 reveal that if only the granular tobacco is compressed, unevenness of the granular tobacco inside the frame 34 can be reliably prevented regardless of the filling weight of the granular tobacco, and that the higher the compression ratio, the less annoying the suction noise is.

Further, Tables 3 to 5 show that for similar compression ratios, the smaller the inner diameter of the frame 34, that is, the smaller the total area of the ventilation openings 37 (area of the openings 119), the more effectively generation of the suction noise is suppressed.

Regarding the evaluation of the suction noise and unevenness shown in Tables 3 to 5, the symbol "*" indicates that the suction noise could not be suppressed enough even though the granular tobacco was even. When actually designing the flavor inhalator, therefore, both suction noise and unevenness need to be taken into consideration.

This will be considered in more detail.

A filling layer of granular tobacco has a flow resistance, and it is thought that a filling layer with a greater flow resistance exhibits more superior reflection and absorption of the suction noise. It has been known that the flow resistance of a filling layer can be expressed by the Kozeny-Carman equation, which can be represented as follows:

$$\text{Flow resistance} = ((1-\text{Porosity}^2)/\text{Porosity}^3) \times (\text{Filling height/Sectional area}) \times \text{Constant} \quad (1)$$

$$\text{Porosity} = (\text{Filling capacity inside frame} - \text{Volume of filled granular tobacco itself})/\text{Filling capacity inside frame}$$

$$\text{Volume of granular tobacco itself} = \text{Filling weight/Apparent density}$$

Figure 14:
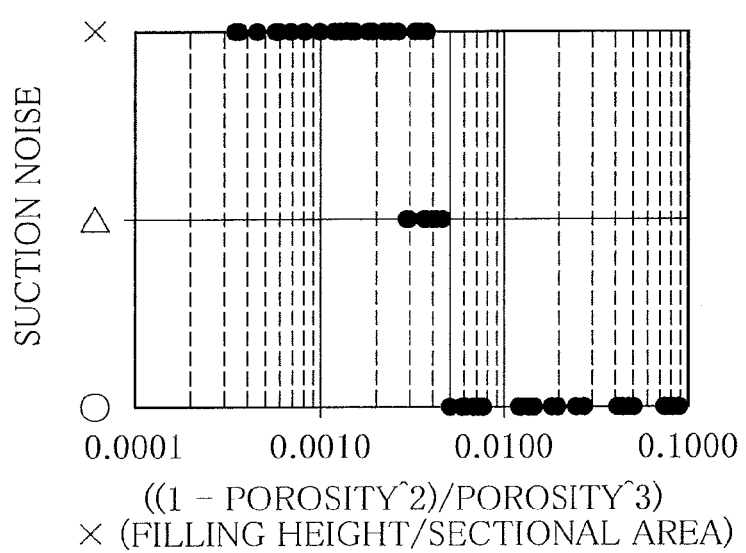
FIG. 14 is a graph showing the relationship between a variable value indicative of flow resistance and suction noise.

Regarding $((1-\text{Porosity}^2)/\text{Porosity}^3) \times (\text{Filling height/Sectional area})$ [1/mm] in Equation (1) as a variable term, the relationship between the variable term and the suction noise was studied, the results being shown in FIG. 14. In FIG. 14, "o", "Δ" and "x" indicate that the suction noise is "not annoying", "somewhat annoying" and "annoying", respectively. FIG. 14 reveals that if the variable term is equal to or higher than 0.005, the suction noise can be reliably suppressed.

Subsequently, the relationship between the pressure loss of the aforementioned air-permeable sheet 39 or air-permeable pouch 86 and the suction noise suppression effect was investigated.

For the purpose of investigation, the suction tester 105 illustrated in FIG. 13 was used with sheets of nonwoven cloth with different pressure losses interposed between the frame 34 and the mesh members 109 and 111 of the suction tester 105. Table 6 below shows the relationship between the nonwoven cloth sheets used and their pressure losses.

TABLE 6

| | Nonwoven cloth | | | | |
|---|---|---|---|---|---|
| | HOP-6H | HOP-10H | HOP-15H | HOP-30H | HOP-45H |
| Pressure loss (mmH$_2$O) | 0 | 0.5 | 1 | 2 | 4 |

The nonwoven cloth sheets shown in Table 6 are all polyolefin nonwoven cloth sheets from Hirose Paper Manufacturing Co., Ltd.

The pressure loss of the nonwoven cloth was evaluated in the following manner:

The suction tester fitted with an empty flavor cartridge was prepared, and the flavor cartridge included a frame with an inner diameter of 20 mm and a height of 5 mm and two sheets of nonwoven cloth attached to the upper and lower surfaces of the frame, respectively. Air was sucked through the suction tester at a flow rate of 1 L/min, and a water-gauge pressure difference was measured. Since the measurement result obtained indicates the total pressure loss of the two nonwoven cloth sheets, each pressure loss shown in Table 6 is ½ of the corresponding measurement result. Specifically, each pressure loss shown in Table 6 indicates the water gauge pressure (mmH$_2$O) of a single nonwoven cloth sheet evaluated at a linear velocity of 0.05 m/s.

Figure 15:
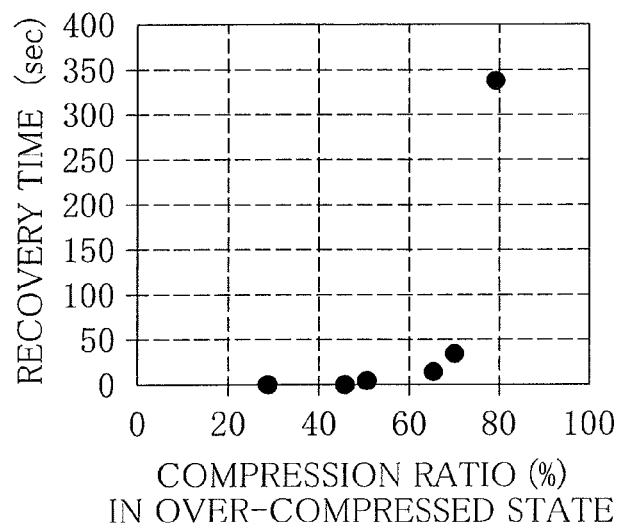
FIG. 15 is a graph showing the relationship between compression ratio of flavor generating material and recovery time.

Table 7 below shows the evaluation results of suction noise suppression effects of the nonwoven cloth sheets, obtained with use of suction testers similar to the suction tester 105 of FIG. 15.

TABLE 7

| | No nonwoven cloth | Pressure loss (mmH$_2$O) of nonwoven cloth | | | | |
|---|---|---|---|---|---|---|
| | | 0 | 0.5 | 1 | 2 | 4 |
| Filling weight 100 mg | | | | | | |
| Φ16 × 3 mm | Δ | Δ | o | o | | |
| Φ18 × 2 mm | Δ | Δ | o | o | | |
| Filling weight 200 mg | | | | | | |
| Φ18 × 5 mm | Δ | Δ | o | o | | |
| Φ20 × 4 mm | Δ | Δ | o | o | | |
| Φ22 × 3 mm | X | X | X | o | | |
| Φ24 × 2 mm | X | X | X | Δ | o | o |
| Φ26 × 2 mm | X | X | X | X | Δ | o |
| Filling weight 300 mg | | | | | | |
| Φ22 × 5 mm | Δ | Δ | o | o | | |
| Φ24 × 4 mm | X | X | o | o | | |
| Φ26 × 3 mm | X | X | X | o | o | |
| Φ28 × 2 mm | X | X | X | Δ | o | o |
| Φ30 × 2 mm | X | X | X | X | Δ | o |

In Table 7, the meanings of "o", "Δ" and "x" are the same as those explained above, and "Φ" indicates the inner diameter of the frame.

As is clear from Table 7, the nonwoven cloth exerts a satisfactory suction noise suppression effect if only it has a pressure loss of 0.5 mmH$_2$O or higher. It is to be noted that the material of the nonwoven cloth is not particularly limited.

Also, in connection with the manufacture of the aforementioned flavor cartridge 30, the over-compressed state of the flavor generating material 32 (flavor pack 87) was verified.

Flavor packs for the verification were prepared, and each flavor pack had a size of 11 mm×50 mm, contained the flavor generating material 32 in an amount of 300 mg, and included an air-permeable pouch of HOP-30H.

Each flavor pack was compressed at a constant rate of 1 mm/s down to a predetermined height and then was kept in the compressed state for five seconds, and after the flavor pack was released from the compression, change in the height of the flavor pack was measured. FIG. 15 shows the relationship between the compression ratio of each flavor pack and the recovery time which the compressed flavor pack required until 75% of the initial height was recovered. The compression ratio is given by the following equation:

Compression ratio (%)=(1−Height of compressed flavor pack/Initial height of flavor pack)×100

Where the required compressed state and the time necessary for the attachment of the upper compression plate 36 are taken into account, the flavor pack needs to be compressed into a sufficiently over-compressed state. Attention should, however, be paid to the fact that if the over-compression is too severe, the flavor pack requires a substantially long recovery time, as is clear from FIG. 15.

On the other hand, in order to obtain a satisfactory suction noise suppression effect by means of the variable term in the aforementioned Equation (1), the compression ratio in the required compressed state needs to be approximately 25% or higher. Taking this into consideration, the recovery time shown in FIG. 15 indicates the time which the flavor pack requires to recover from the over-compressed state to the required compressed state.

Thus, in view of the time necessary for the attachment of the upper compression plate 36, the compression ratio in the over-compressed state should be 50% or higher, but if the compression ratio exceeds 80%, crushing of the granular tobacco takes place. Consequently, the compression ratio in the over-compressed state should preferably be higher than or equal to 50% and be lower than or equal to 80%.

The flavor inhalator of the present invention is not limited to the foregoing first and second embodiments and may be modified in various ways. In the following, modifications of the flavor inhalator will be described. The flavor cartridges 30 of the flavor inhalators according to the modifications may either be of the type used in the first embodiment or the type used in the second embodiment.

Figure 16:
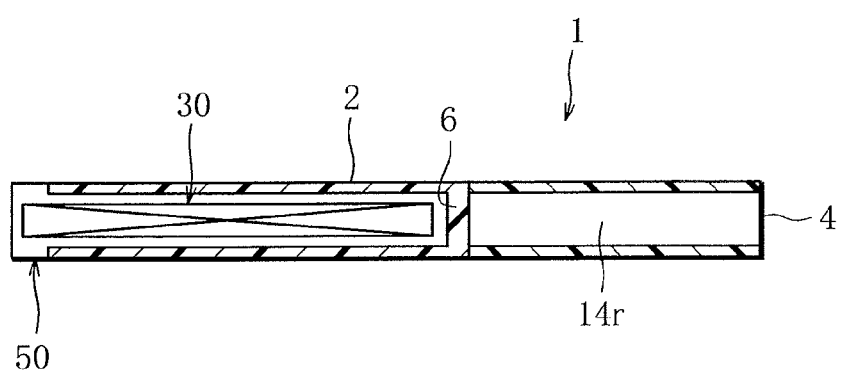
FIG. 16 is a sectional view of a flavor inhalator according to a modification.

The flavor inhalator 1 illustrated in FIG. 16 includes a generally T-shaped flavor cartridge 30. Specifically, the flavor cartridge 30 has a protuberance 50 protruding from one end thereof on both sides. The protuberances 50 is located at the front end of the holder 2 and has a width nearly equal to the diameter of the holder 2.

On the other hand, the longitudinal grooves 8 of the holder 2 are bent at the front end of the holder 2, and the bent portions open in the outer peripheral surface of the holder 2, thereby permitting the protuberance 50 to be received in the bent portions. The user can pinch the protuberance 50 of the flavor cartridge 30, so that the flavor cartridge 30 can be handled with ease, facilitating the attachment and detachment of the flavor cartridge 30 to and from the holder 2.

Figure 17:
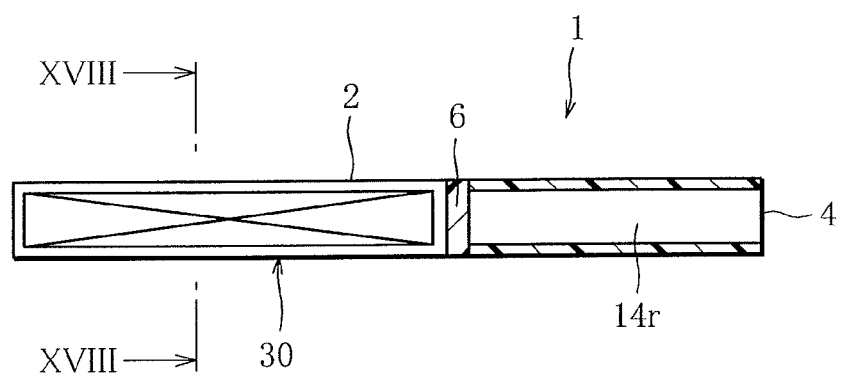
FIG. 17 is a sectional view of a flavor inhalator according to another modification.
Figure 18:
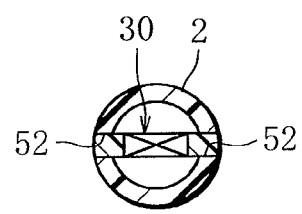
FIG. 18 is a sectional view of the flavor inhalator taken along line VIII-VIII in FIG. 17.

The holder 2 of the flavor inhalator 1 shown in FIGS. 17 and 18 has a pair of guide slots 52, in place of the pair of longitudinal grooves 8. The guide slots 52 are set apart from each other in a diametrical direction of the holder 2 with the axis of the holder 2 located therebetween, extend from the front end wall of the holder 2 to the partition wall 6 in parallel with each other, and allows the inside of the holder 2 to communicate with the outside.

In this case, the flavor cartridge 30 may have a width almost equal to the diameter of the holder 2. Thus, when the opposite side edges of the flavor cartridge 30 are inserted into the respective guide slots 52, the opposite side faces of the frame 34 form part of the outer peripheral wall of the holder 2 (see FIG. 18). This flavor cartridge 30 enables the user to easily confirm whether the flavor cartridge 30 is set in the holder 2 or not.

Figure 19:
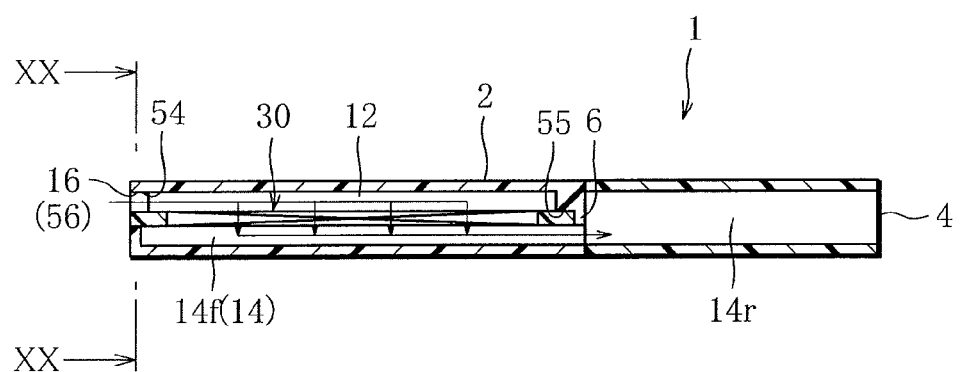
FIG. 19 is a sectional view of a flavor inhalator according to still another modification.
Figure 20:
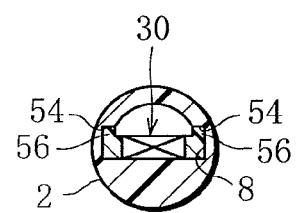
FIG. 20 is a sectional view of the flavor inhalator taken along line X-X in FIG. 19.

In the flavor inhalator illustrated in FIGS. 19 and 20, each longitudinal groove 8 has front and rear hold surfaces 54 and 55 at its front and rear ends, respectively, for holding the flavor cartridge 30. The front hold surface 54 is formed by recessing the upper groove wall of each longitudinal groove 8, and the rear hold surface 55 is formed by extending the rear end of each longitudinal groove 8 into the partition wall 6.

On the other hand, the frame 34 of the flavor cartridge 30 has a pair of protrusions 56 formed at its front edge and associated with the respective front hold surfaces 54. The protrusions 56 protrude from the frame 34 and are set apart from each other in the width direction of the frame 34. When the flavor cartridge 30 is inserted into the holder 2 along the longitudinal grooves 8, the rear end of the frame 34 is pressed by the rear hold surfaces 55, and the protrusions 56 of the frame 34 are pressed by the respective front hold surfaces 54. As a result, the frame 34, that is, the flavor cartridge 30, is securely held inside the holder 2.

Figure 21:
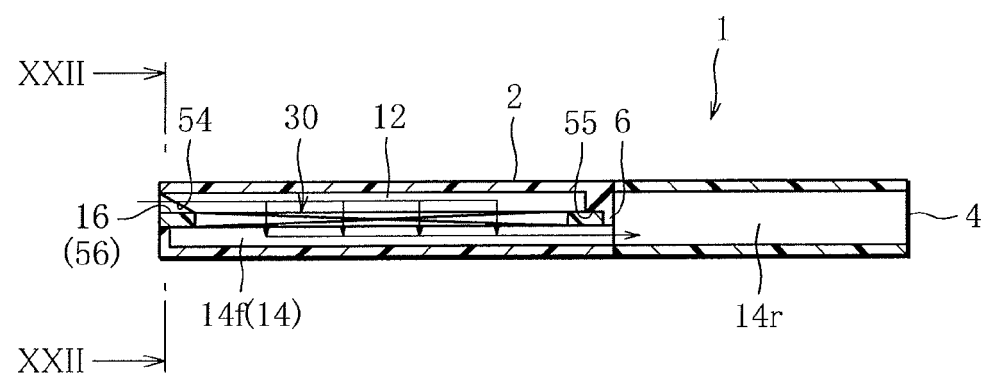
FIG. 21 is a sectional view of a flavor inhalator according to a further modification.
Figure 22:
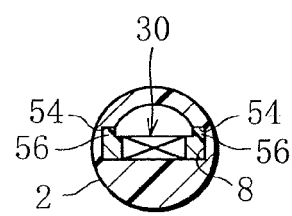
FIG. 22 is a sectional view of the flavor inhalator taken along line XII-XII in FIG. 21.

In the flavor inhalator 1 illustrated in FIGS. 21 and 22, the front hold surfaces 54 and the protrusions 56 cooperatively constitute a wedge structure. The wedge structure ensures that the frame 34, that is, the flavor cartridge 30, is more securely held within the holder 2.

Figure 23:
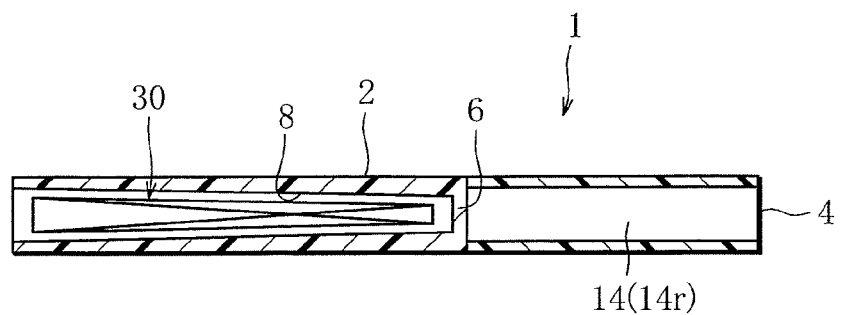
FIG. 23 is a sectional view of a flavor inhalator according to another modification.

The flavor inhalator 1 shown in FIG. 23 includes the flavor cartridge 30 which is shaped like a wedge as a whole. Specifically, the width of the flavor cartridge 30 decreases with the increasing distance from the front end toward the rear end. On the other hand, the distance between the bottom walls of the two longitudinal grooves 8 gradually decreases with the increasing distance from the front end of the holder 2 toward the rear end, namely, toward the partition wall 6, so that the longitudinal groove 8 may correspond in shape to the wedge-like shape of the flavor cartridge 30.

Figure 24:
FIG. 24 is a side view of a flavor inhalator according to still another modification.

The flavor cartridge 30 for the flavor inhalator, illustrated in FIG. 24, has a thickness gradually decreasing with the increasing distance from the front end toward the rear end. The groove width of each of the longitudinal grooves 8 of the holder 2 also gradually decreases with the increasing distance from the front end toward the rear end, so as to correspond to the thickness of the flavor cartridge 30. Thus, when the flavor cartridge 30 is inserted in its entirety into the holder 2, the both side edges of the flavor cartridge 30 come into close contact with the respective longitudinal grooves 8, thus preventing the flavor cartridge 30 from clattering inside the holder 2.

Figure 25:
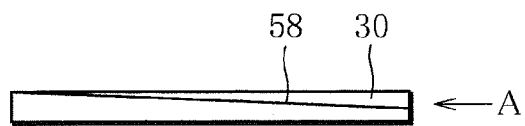
FIG. 25 is a side view of a flavor inhalator according to a further modification.
Figure 26:
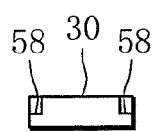
FIG. 26 is a front view of a flavor cartridge, as viewed from a direction indicated by arrow A in FIG. 25.

The flavor cartridge 30 for the flavor inhalator, illustrated in FIGS. 25 and 26, has wedge surfaces 58 formed only on the upper sides of the opposite side edge portions thereof. The thickness of each wedge portion 58 gradually decreases with the increasing distance from the front end of the flavor cartridge 30 toward the rear end. This permits the flavor cartridge 30 to have au upper surface parallel with the axis of the holder 2, except for the opposite side edges. The flavor inhalator according to this modification guarantees that the flavor cartridge 30 is securely held inside the holder 2 without entailing reduction in the filling content of the tobacco material in the flavor cartridge 30.

Figure 27:
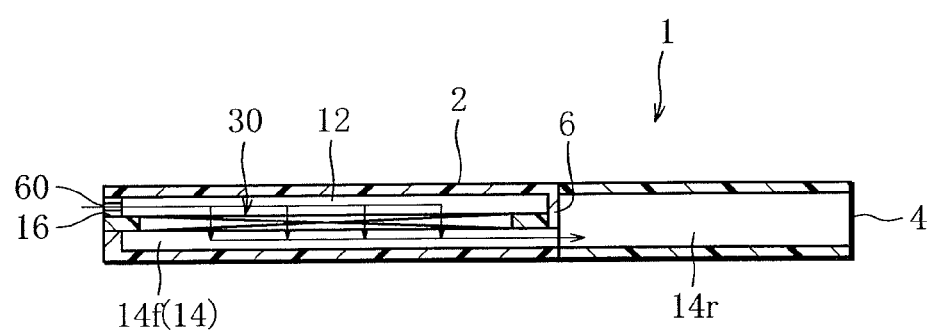
FIG. 27 is a sectional view of a flavor inhalator according to another modification.

The flavor inhalator 1 illustrated in FIG. 27 further includes an air-permeable filter 60 arranged in the ambient air admission opening 16. The filter 60 absorbs the suction noise generated by the flow of air in the upstream region 12 of the holder 2 when the user inhales, and also serves to remove impurities contained in the air. The filter 60 may alternatively be configured to occupy the whole upstream region 12.

Figure 28:
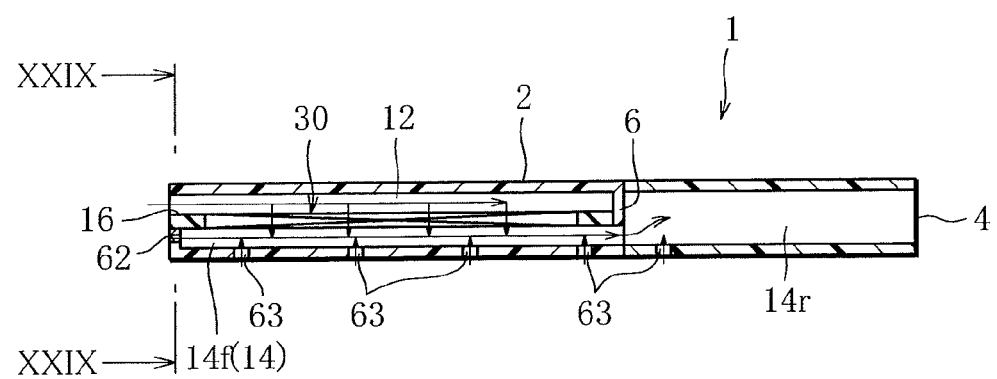
FIG. 28 is a sectional view of a flavor inhalator according to still another modification.
Figure 29:
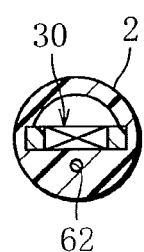
FIG. 29 is a sectional view taken along line XIX-XIX in FIG. 28.

The holder 2 of the flavor inhalator 1 shown in FIGS. 28 and 29 further includes ambient air admission openings 62 and 63, in addition to the ambient air admission opening 16. The ambient air admission opening 62 allows the downstream region 14 to communicate directly with the outside of the holder 2. On the other hand, the ambient air admission openings 63 are distributed over a portion of the peripheral wall of the holder 2 corresponding to the downstream region 14. Specifically, the ambient air admission openings 63 are spaced from each other in the axial direction of the holder 2 and allow the downstream region 14 to directly communicate with the outside of the holder 2.

Thus, when the user inhales, ambient air flows into the holder 2 through the ambient air admission openings 16, 62 and 63. The inflow of air through the ambient air admission openings 62 and 63 decreases the velocity of the air flowing inside the upstream region 12, with the result that generation of the suction noise in the upstream region 12 is effectively suppressed.

Figure 30:
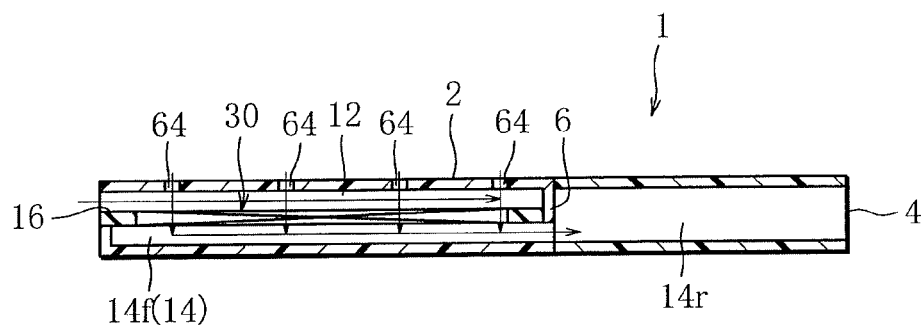
FIG. 30 is a sectional view of a flavor inhalator according to another modification.

The holder 2 of the flavor inhalator 1 shown in FIG. 30 has a plurality of ambient air admission openings 64 formed through a portion of the peripheral wall thereof corresponding to the upstream region 12. The ambient air admission openings 64 are spaced from each other in the axial direction of the holder 2 and allow the upstream region 12 to communicate directly with the outside of the holder 2. Also in this case, the flow of air from the ambient air admission openings 64 into the upstream region 12 reduces the velocity of the air flowing in the upstream region 12, so that generation of the suction noise can be effectively suppressed.

Figure 31:
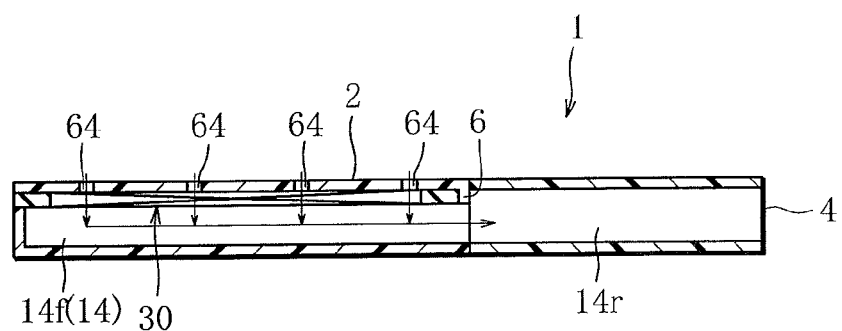
FIG. 31 is a sectional view of a flavor inhalator according to still another modification.

The flavor cartridge 30 of the flavor inhalator 1 illustrated in FIG. 31 differs from the one illustrated in FIG. 30 in that the flavor cartridge 30 is arranged so as to occupy the whole upstream region 12. The flavor cartridge 30 has a semi-cylindrical shape corresponding to the upstream region 12 and is disposed in contact with a portion of the inner peripheral surface of the holder 2 defining the upstream region 12.

With this flavor cartridge 30 for the flavor inhalator, the cross-sectional area of the downstream region 14 can be increased. Since the flow velocity of the air flowing in the downstream region 14 can be reduced as a result, the suction noise accompanying the user's inhalation is suppressed. Also, since the flavor cartridge 30 occupies the whole upstream region 12, the flow velocity of the air passing through the flavor cartridge 30 does not become high. Thus, suction noise is of course not generated in the upstream region 12.

Figure 32:
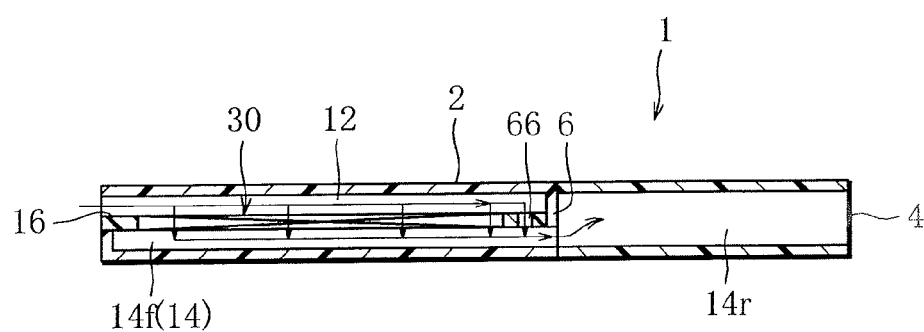
FIG. 32 is a sectional view of a flavor inhalator according to yet another modification.

The flavor cartridge 30 of the flavor inhalator 1 illustrated in FIG. 32 further includes a communication hole 66. The communication hole 66 is formed at the rear end of the frame 34 and allows the upstream and downstream regions 12 and 14 to communicate with each other. The communication hole 66 permits air to flow from the upstream region 12 into the downstream region 14 without passing through the flavor cartridge 30, and therefore, the amount of air flowing through the downstream region 14, that is, the air flow velocity, can be reduced, making it possible to suppress generation of the suction noise in the downstream region 14. The communication hole 66 may alternatively be formed at the front end of the frame 34, though not illustrated. In this case, the amount of air flowing through the upstream region 12, that is, the air flow velocity, can be reduced, whereby generation of the suction noise in the upstream region 12 can be effectively suppressed.

Figure 33:
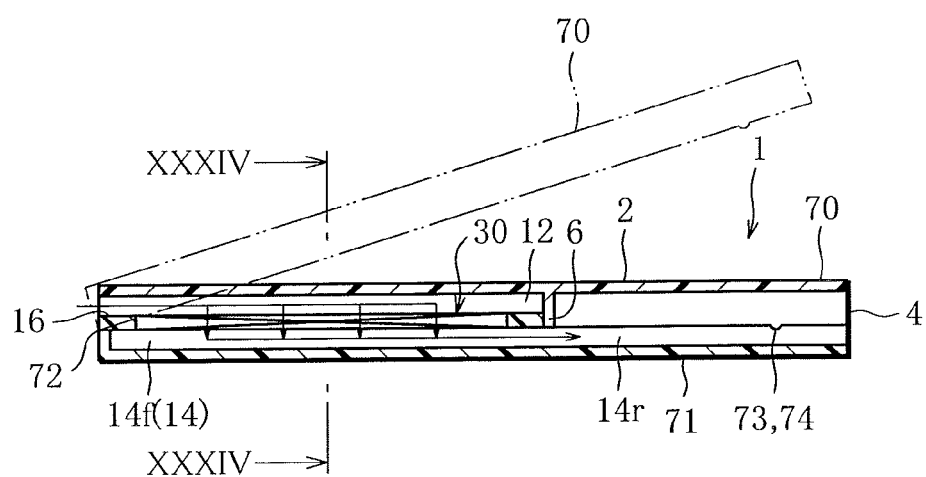
FIG. 33 is a sectional view of a flavor inhalator according to a further modification.
Figure 34:
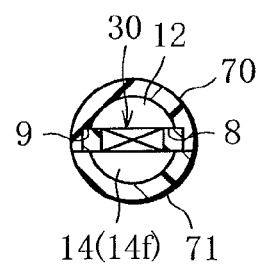
FIG. 34 is a sectional view of the flavor inhalator taken along line XIV-XXIV in FIG. 33.

The flavor inhalator 1 illustrated in FIGS. 33 and 34 is provided with the holder 2 of opening/closing type. The holder 2 is made up of an upper half pipe 70 and a lower half pipe 71. The upper half pipe 70 includes the upstream region 12, the partition wall 6, part of the downstream region 14, and the ambient air admission opening 16. The lower half pipe 71 includes the remainder of the downstream region 14.

The upper and lower half pipes 70 and 71 have lower and upper open edge pairs, respectively, extending along the axis of the holder 2. When the upper open edges are superposed on the respective lower open edges, the upper and lower open edges cooperatively form the aforementioned longitudinal grooves 8. Specifically, each upper open edge has a cut forming part of the longitudinal groove 8, and each lower open edge has a cut forming the remaining part of the longitudinal groove 8.

Further, the front ends of the upper and lower half pipes 70 and 71 are connected together by a living hinge 72. The holder 2 is opened and closed as the upper half pipe 70 is turned about the living hinge 72 relative to the lower half pipe 71. In FIG. 23, the dot-dot-dash lines indicate the upper half pipe 70 of the holder 2 in the open position.

Projections 74 are formed, for example, on the rear end portions of the open edges of the upper half pipe 70, and recesses 73 associated with the respective projections 74 are formed in the open edges of the lower half pipe 71. When the holder 2 is in the closed position, that is, when the open edges of the upper and lower half pipes 70 and 71 are butted against each other, the projections 74 are received in the respective recesses 73. The engagement of the projections 74 with the recesses 73 prevents the holder 2 from opening accidentally and serves to stably keep the holder 2 in the closed state.

When the holder 2 is in the closed position as illustrated in FIG. 34, the flavor cartridge 30 is held between the upper and lower half pipes 70 and 71 with the opposite side edges of the frame 34 received in the respective longitudinal grooves 8. Thus, the flavor cartridge 30 is immovably held within the holder 2 and does not clatter inside the holder 2. Since the holder 2 can be opened and closed as needed as stated above, replacement of the flavor cartridge 30 is easy.

Figure 35:
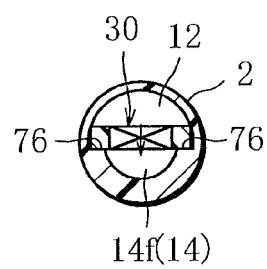
FIG. 35 is a sectional view of a flavor inhalator according to another modification.

The holder 2 for the flavor inhalator 1, shown in FIG. 35, has a pair of rest surfaces 76, in place of the pair of longitudinal grooves 8. The rest surfaces 76 face the upstream region 12 in the holder 2 and horizontally extend along the axis of the holder 2.

Specifically, the upper semi-circumferential surface of the holder 2 forming the upstream region 12 has a radius of curvature larger than that of the lower semi-circumferential surface of the holder 2 forming the front flow section 14$f$. When the flavor cartridge 30 is set on the rest surfaces 76, the opposite side edges of the flavor cartridge 30 are held between the respective rest surfaces 76 and the upper semi-circumferential surface of the holder 2. That is, the upper semi-circumferential surface of the holder 2 serves to press the flavor cartridge 30 against the rest surfaces 76, with the result that the flavor cartridge 30 is securely held within the holder 2.

Figure 36:
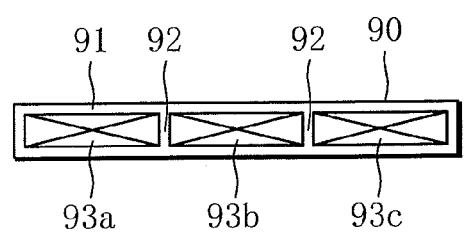
FIG. 36 is a plan view of a flavor cartridge according to another modification.

A frame 91 of a flavor cartridge 90 illustrated in FIG. 36 is similar to the aforementioned frame 34 but differs therefrom in that the frame 91 has two ribs 92 therein. The ribs 92 partition the interior of the frame 91 into three regions. These regions are arranged in a row along the longitudinal direction of the flavor cartridge 90 and accommodate flavor generating materials 93$a$, 93$b$ and 93$c$, respectively. The flavor generating materials 93$a$, 93$b$ and 93$c$ are kept out of contact with each other and capable of emitting respective different flavor components. Further, the flavor generating materials 93*a*, 93*b* and 93*c* may give off other flavor components than the flavor component of tobacco material.

Figure 37:
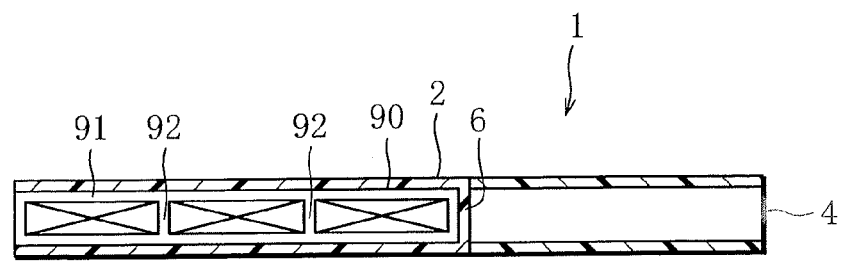
FIG. 37 is a horizontal sectional view of a flavor inhalator provided with the flavor cartridge of FIG. 36.
Figure 38:
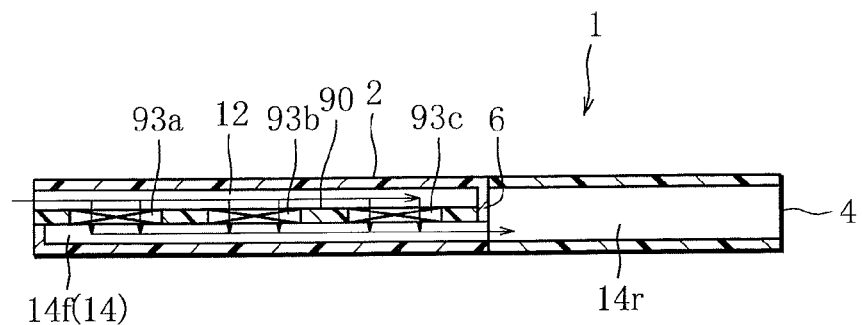
FIG. 38 is a longitudinal sectional view of the flavor inhalator of FIG. 37.

When the flavor cartridge 90 is set in the holder 2 as illustrated in FIGS. 37 and 38, the flavor generating materials 93*a*, 93*b* and 93*c* are lined up along the axis of the holder 2. As the user inhales through the mouthpiece end 4, air introduced into the upstream region 12 of the holder 2 passes through any one of the flavor generating materials 93*a*, 93*b* and 93*c* and is mixed in the front flow section 14*f* of the downstream region 14. The air thus mixed contains the respective flavor components of the flavor generating materials 93*a*, 93*b* and 93*c* and flows to the mouthpiece end 4 through the rear flow section 14*r* of the downstream region 14. Consequently, the user can enjoy the flavor components of the three different kinds of flavor generating materials 93*a*, 93*b* and 93*c* at the same time. The combination of the flavor generating materials may be changed so as to suit users' tastes.

Figure 39:
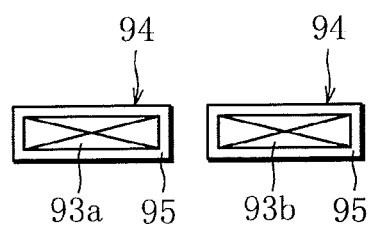
FIG. 39 is a plan view of a flavor cartridge according to another modification.

Each frame 95 of a flavor cartridge 94 shown in FIG. 39 has a length approximately half the length of the frame 91. Thus, two flavor cartridges 94 containing respective different flavor generating materials 93*a* and 93*b* are prepared and set in tandem in the holder 2. Also in this case, the user can enjoy the flavor components of different flavor generating materials.

Figure 40:
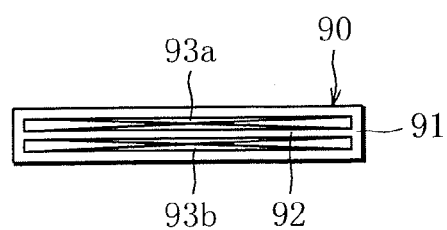
FIG. 40 is a plan view of a flavor cartridge according to still another modification.

The frame 91 of the flavor cartridge 90 shown in FIG. 40 has a single rib 92. The rib 92 extends in the center of the frame 91 along the axis of the frame 91 and partitions the interior of the frame 91 into two, upper and lower regions. Thus, the flavor cartridge 90 also is capable of accommodating the flavor generating materials 93*a* and 93*b* while keeping the materials 93*a* and 93*b* out of contact with each other. In this case, the flavor generating materials 93*a* and 93*b* are arranged parallel with each other along the axis of the frame 91.

Figure 41:
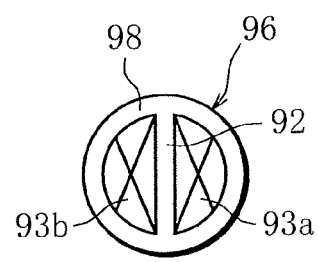
FIG. 41 is a front view of a flavor cartridge according to yet another modification.

A flavor cartridge 96 illustrated in FIG. 41 includes a cylindrical sleeve 98 having a rib 92 therein. The rib 92 extends within the sleeve 98 along its axis and partitions the interior of the sleeve 98 into two, right and left regions. Also with this flavor cartridge 96, two different kinds of flavor generating materials 93*a* and 93*b* can be accommodated while being kept out of contact with each other.

Figure 42:
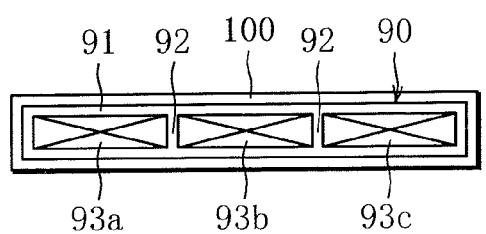
FIG. 42 is a plan view of a flavor cartridge according to a further modification.
Figure 43:
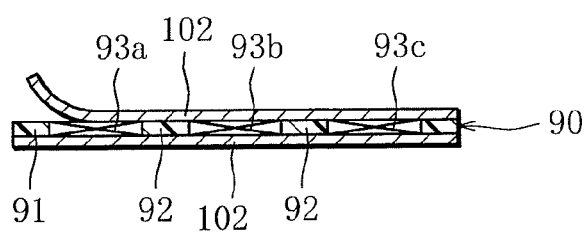
FIG. 43 is a sectional view of a flavor cartridge according to a still further modification.

It is necessary that the flavor component contained in the flavor generating material 93 should be prevented from volatilizing during storage of the flavor cartridge. Accordingly, as illustrated in FIG. 42, the flavor cartridge 90 may further include an air-impermeable wrapper 100. The wrapper 100 unsealably seals in the flavor generating materials 93*a*, 93*b* and 93*c* together with the frame 91. Alternatively, as illustrated in FIG. 43, only the exposed surfaces of the flavor generating materials 93 exposed from the frame 91 may be airtightly covered with a peelable seal film 102.

The seal film 102 may alternatively cover each of the flavor generating materials 93*a*, 93*b* and 93*c* separately from one another.

Figure 44:
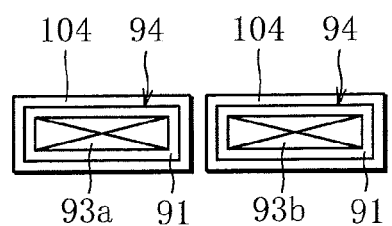
FIG. 44 is a plan view of a flavor cartridge according to a further modification.

Two flavor cartridges 94 illustrated in FIG. 44 accommodate respective flavor generating materials and are each wrapped in an air-impermeable wrapper 104 in the form of a pillow. It is therefore possible to prevent the flavor component of the flavor generating material contained in one flavor cartridge 94 from deteriorating the flavor generating material contained in the other flavor cartridge 94 during storage of the flavor cartridges 94. The flavor cartridge 94 may be sealed in other ways than the pillow wrap, such as blister packaging or packaging using resealable seals.

EXPLANATION OF REFERENCE SIGNS

1: flavor inhalator
2: holder
4: mouthpiece end
6: partition wall
8: longitudinal groove
12: upstream region
14: downstream region
16: ambient air admission opening
30: flavor cartridge
32: flavor generating material
34: frame
36: compression plate
37: ventilation opening
39: air-permeable sheet
40: manufacturing apparatus
42: supporting base
44: guide frame
46: pusher
50: protuberance
52: guide slot
54, 55: hold surface (pressing surface)
56: protrusion
58: wedge surface
60: filter
62: ambient air admission opening (air inlet hole)
63: ambient air admission opening (air inlet hole)
64: ambient air admission opening (air inlet hole)
66: communication hole
70: upper half pipe
71: lower half pipe
72: living hinge
73: recess
74: projection
76: rest surface
86: air-permeable pouch
87: flavor pack
89: measuring device
90: flavor cartridge
91: frame
92: rib
93: flavor generating material
94: flavor cartridge
95: frame
96: flavor cartridge
98: sleeve
100: wrapper
102: seal film
104: wrapper

The invention claimed is:
1. A non-heating flavor inhalator comprising:
a hollow holder having an axis, the holder including a front end, a rear end serving as a mouthpiece end, an ambient air admission opening, and a flow passage defined in the holder and configured to guide ambient air introduced from the ambient air admission opening to the mouthpiece end; and
a flavor cartridge having air permeability and arranged in the holder so as to extend inside the holder from the front end toward the mouthpiece end along the axis of the holder, the flavor cartridge dividing the flow passage into a downstream region extending from the flavor cartridge to the mouthpiece end, and an upstream region communicating with the ambient air admission opening and located contiguous with the flavor cartridge, wherein the flavor cartridge includes:

a frame, a granular flavor generating material filled in the frame and capable of emitting a flavor component without being ignited, the flavor generating material containing granular tobacco obtained by shredding or pulverizing tobacco leaf, and a compression device configured to keep the flavor generating material in a compressed state and filled within the frame while ensuring air permeability of the flavor cartridge, wherein the frame holds the granular flavor generating material therein, and the flavor component emitted from the flavor generating material is contained in the ambient air introduced in the flow passage and then supplied to the mouthpiece end, together with the ambient air, and wherein the compression device includes a pair of compression elements configured to compress the flavor generating material in a direction perpendicular to the axis of the holder, each of the compression elements having at least one ventilation opening formed therein to secure air permeability of the flavor cartridge.

2. The non-heating flavor inhalator according to claim 1, wherein the ventilation opening in one of the compression elements partly overlaps with the ventilation opening in the other of the compression elements, as viewed in the direction of compression of the flavor generating material.

3. The non-heating flavor inhalator according to claim 2, wherein the flavor generating material is filled in such a manner that a flow resistance of the flavor generating material after compression, expressed by a formula:

$$((1-\text{Porosity}^2)/\text{Porosity}^3) \times (\text{Filling height/Sectional area})$$

is equal to or higher than 0.005.

4. The non-heating flavor inhalator according to claim 1, wherein the flavor cartridge further includes an air-permeable pouch wrapping the flavor generating material therein.

5. The non-heating flavor inhalator according to claim 4, wherein the air-permeable pouch has a pressure loss of 0.5 mmH$_2$O or higher.

6. The non-heating flavor inhalator according to claim 1, wherein:

the flavor generating material is filled directly in the frame, and the flavor cartridge further includes an air-permeable element covering the ventilation openings of the compression elements.

7. The non-heating flavor inhalator according to claim 6, wherein the air-permeable element has a pressure loss of 0.5 mmH$_2$O or higher.

8. The non-heating flavor inhalator according to claim 1, wherein the flavor cartridge further includes a plurality of independent accommodation regions configured to accommodate different kinds of flavor generating materials.

9. The non-heating flavor inhalator according to claim 8, wherein the flavor cartridge further includes a wrapper airtightly covering the accommodation regions in such a manner that the accommodation regions can be opened and closed.

10. A non-heating flavor inhalator comprising:

a hollow holder having an axis, the holder including a front end, a rear end serving as a mouthpiece end, an ambient air admission opening, and a flow passage defined in the holder and configured to guide ambient air introduced from the ambient air admission opening to the mouthpiece end; and a flavor cartridge having air permeability and arranged in the holder so as to extend inside the holder from the front end toward the mouthpiece end along the axis of the holder, the flavor cartridge dividing the flow passage into a downstream region extending from the flavor cartridge to the mouthpiece end, and an upstream region communicating with the ambient air admission opening and located contiguous with the flavor cartridge, wherein the flavor cartridge includes a frame, a granular flavor generating material filled in the frame and capable of emitting a flavor component without being ignited, the flavor generating material containing granular tobacco obtained by shredding or pulverizing tobacco leaf, and a compression device configured to keep the flavor generating material in a compressed state while ensuring air permeability of the flavor cartridge, wherein the compression device includes a pair of compression elements configured to compress the flavor generating material in a direction perpendicular to the axis of the holder, each of the compression elements having a plurality of ventilation openings formed therein to secure air permeability of the flavor cartridge.

* * * * *